United States Patent [19]

Yeager

[11] 4,379,029

[45] Apr. 5, 1983

[54] METHOD OF MEASURING METALLIC CATION AND WATER TRANSPORT NUMBERS FOR CATION EXCHANGE HYDRAULICALLY IMPERMEABLE MEMBRANES AND TEST CELL THEREFOR

[75] Inventor: Howard L. Yeager, Calgary, Canada

[73] Assignee: Olin Corporation, New Haven, Conn.

[21] Appl. No.: 301,071

[22] Filed: Sep. 10, 1981

[51] Int. Cl.³ .................. G01N 27/28; G01N 27/40
[52] U.S. Cl. .................. 204/1 T; 204/261; 204/415
[58] Field of Search .......... 204/261, 195 R, 1 T, 204/252, 273; 324/425

[56] References Cited

U.S. PATENT DOCUMENTS 4,090,924  5/1978  Bon .................. 204/1 T

OTHER PUBLICATIONS

M. Maksimishin et al., Industrial Laboratory, (Trans. of: Zavod. Lab., (USSR), vol. 39, No. 10, pp. 1674-1675, Oct. 1973.

Primary Examiner—G. L. Kaplan
Attorney, Agent, or Firm—Arthur E. Oaks; Donald F. Clements

[57]  ABSTRACT

An electrolytic membrane transport cell adaptable to experimental use for the purpose of accurately measuring simultaneously cation transport and water transport numbers (mol/Faraday) under operating conditions similar to those used in commercial chlor-alkali membrane cells. The cell comprises a pair of half cells each containing a truncated conical chamber adapted to matingly fit together, when abutted at their apexes, and to form a cell, said cell being adapted to hold a permselective membrane which is sealingly supported between said half cells so as to create separate anode and cathode sections, electrode means, heating means, stirring means and electrolyte inlet means. When used in conjunction with radioactive tracer techniques considerable improvements in the accuracy and ease with which transport phenomena can be studied are possible.

23 Claims, 9 Drawing Figures

METHOD OF MEASURING METALLIC CATION AND WATER TRANSPORT NUMBERS FOR CATION EXCHANGE HYDRAULICALLY IMPERMEABLE MEMBRANES AND TEST CELL THEREFOR

BACKGROUND OF THE INVENTION

The present invention relates generally to membrane type electrolytic cells for the production of chlorine, alkali metal hydroxides and hydrogen and more particularly to a cell which is adapted for experimental studies.

Chlorine and caustic are essential, large volume commodities used in all industrial societies. They are produced almost entirely electrolytically from aqueous solutions of alkali metal chlorides with the largest portion of such production coming from mercury and diaphragm cells. With the advent of technological advances such as dimensionally stable anodes, high activity catalytic cathodic materials and cation exchange, hydraulically impermeable permselective membranes, considerable improvements have been made in both product quality and energy efficiency. However, the complicated chemical structure of these membranes and their relative fragility make it difficult to optimize production parameters. For this, smaller cells are used to determine basic membrane characteristics, particularly their cationic and water transfer numbers and their dynamic properties under conditions typical of an operating cell, such as concentrated solution environments, elevated temperatures and high current densities must be used.

A rather extensive literature exists on the determination of ionic and water transport numbers for ion exchange membranes. For cationic transport both Hittorf-type electrolysis experiments and indirect emf methods have been used. In similar fashion, membrane water transport numbers can be measured by electrolysis techniques or by streaming potential techniques. Aside from the systematic discrepancies which have been observed between emf and the true electrolysis results, the former techniques do not lend themselves to studies using a high current density.

Electrolysis methods based on measuring changes in either electrolytic solution volume or weight are known. Volume methods are generally more convenient, but are susceptible to error due to membrane movement and are difficult to use at elevated temperatures. With this approach, even in carefully performed experiments, the best measurements at conditions of room temperature and low current density reported determinations of potassium ion transport numbers had an average relative standard deviation of 6%.

The need to create a measurable concentration change during electrolysis with this approach presents a further problem for cationic transport number measurements in concentrated solution environments. If concentration changes are kept small, it is difficult to obtain sufficient accuracy in solution analysis to obtain a reliable result. If larger concentration changes are produced, such membrane properties as water and electrolyte content are altered with the result that interpretation of the results become considerably more difficult.

It has been shown that the use of radiotracer techniques can be effective in largely removing the problem of concentration changes in the measurement of membrane transport parameters. These techniques, when applied in the improved test cell described herein, have led to a considerable improvement in the measurement of membrane characteristics under conditions typical of those used in production cells.

SUMMARY OF THE INVENTION

The apparatus of the present invention is an electrolytic membrane transport test cell adaptable to experimental use for the purpose of accurately measuring simultaneously cation transport and water transport numbers (mol/Faraday) under operating conditions similar to those used in commercial chlor-alkali membrane cells. Thus, it is capable of operating at temperatures up to about 100° C. and at chloride or caustic solution concentrations up to about 45%.

As disclosed, the preferred embodiment of the cell comprises two half cells, each of which contains a horizontally disposed, inwardly directed, truncated right conical chamber and an electrode. A full cell is formed by joining, as by bolting or clamping, an anode and a cathode half cell such that the truncated apex ends of the conical chambers are aligned to abut each other to form a biconic or dumb bell shaped electrolysis cell. A permselective membrane is sealingly suspended between the two half cells to separate them into anodic and cathodic compartments. Each half cell further contains stirring means and heating means to allow precise and efficient achievement of uniform temperatures and solution concentrations. In addition, both half cells contain means for introducing electrolyte and a radioactive tracer.

Thus, it is the principal object of the subject invention to provide an improved membrane test cell which provides data on cation and water transport through semipermeable membranes of the types used in commercial chlor-alkali cells more quickly and accurately than heretofore possible.

It is a further object of the subject invention to provide a membrane test cell which is readily adaptable to testing a wide variety of membrane materials under conditions resembling those used in commercial chlor-alkali cells.

Those and other objects and further scope of applicability of the present invention will become apparent from a reading of the detailed description to follow, taken in conjunction with the accompanying drawings.

DETAILED DESCRIPTION OF THE INVENTION

Figure 1:
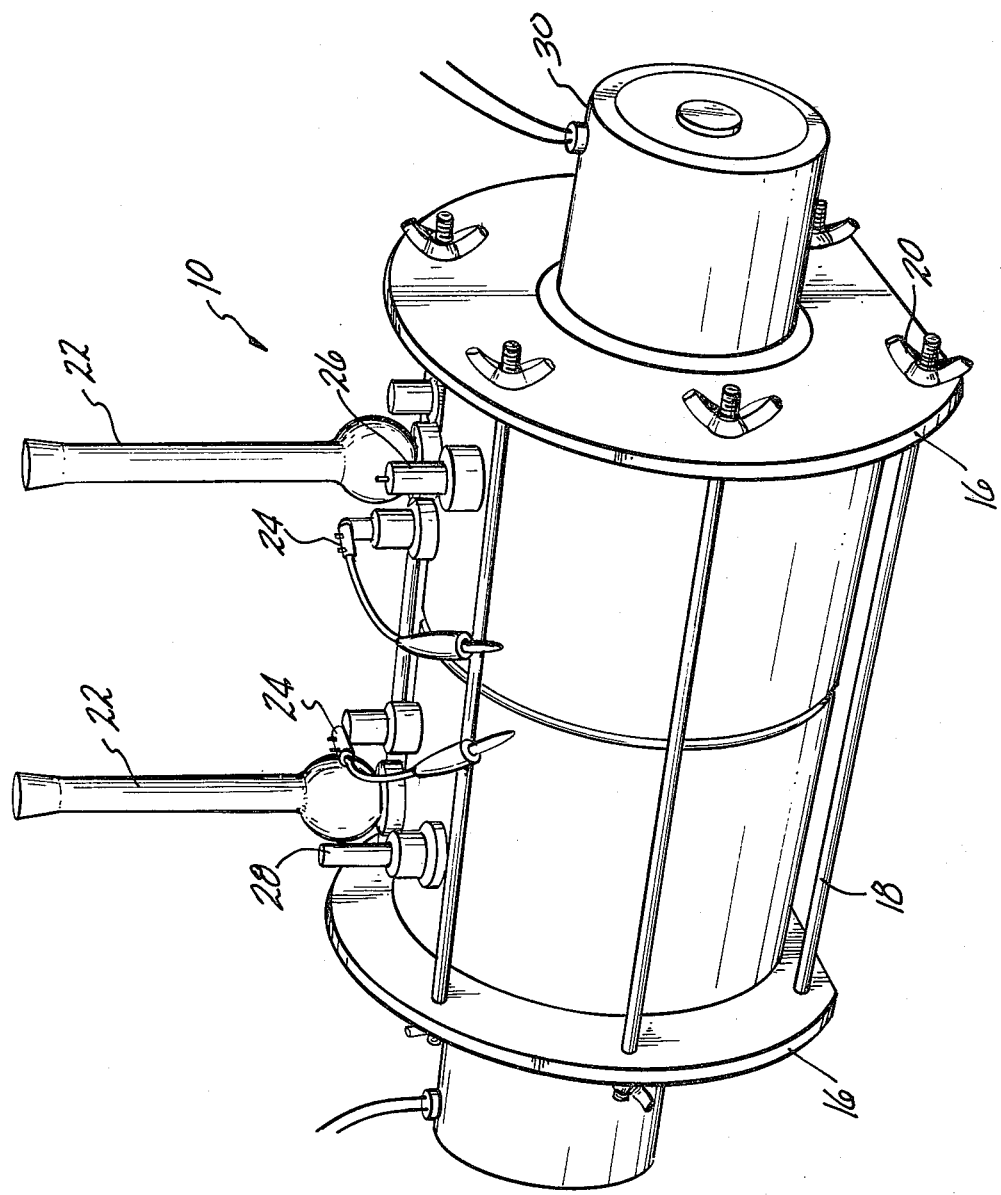
FIG. 1 is an isometric view of a membrane test cell according to the present invention.
Figure 2:
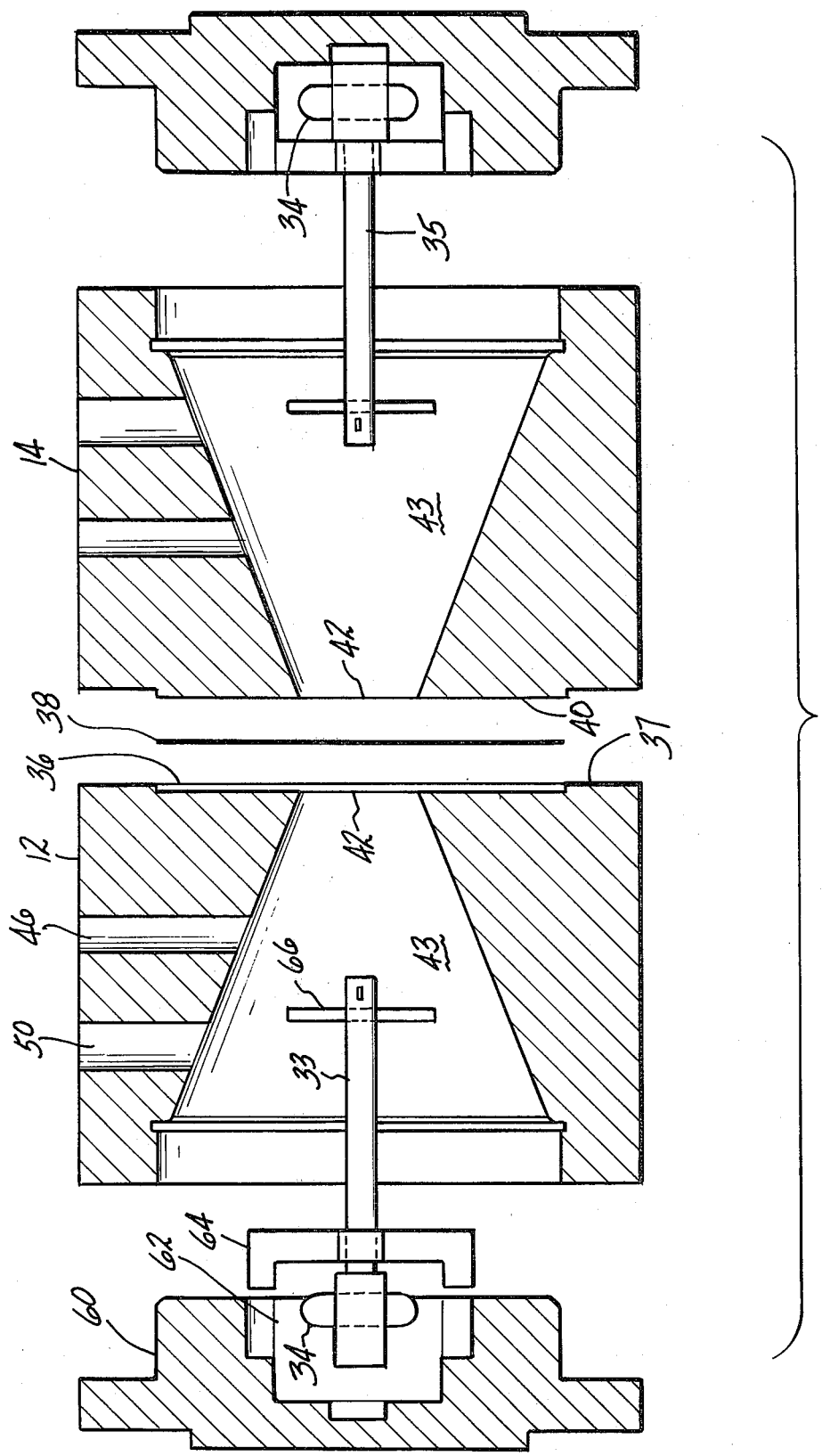
FIG. 2 is an exploded cross sectional view of the test cell of FIG. 1 taken along line 2—2.
Figure 3:
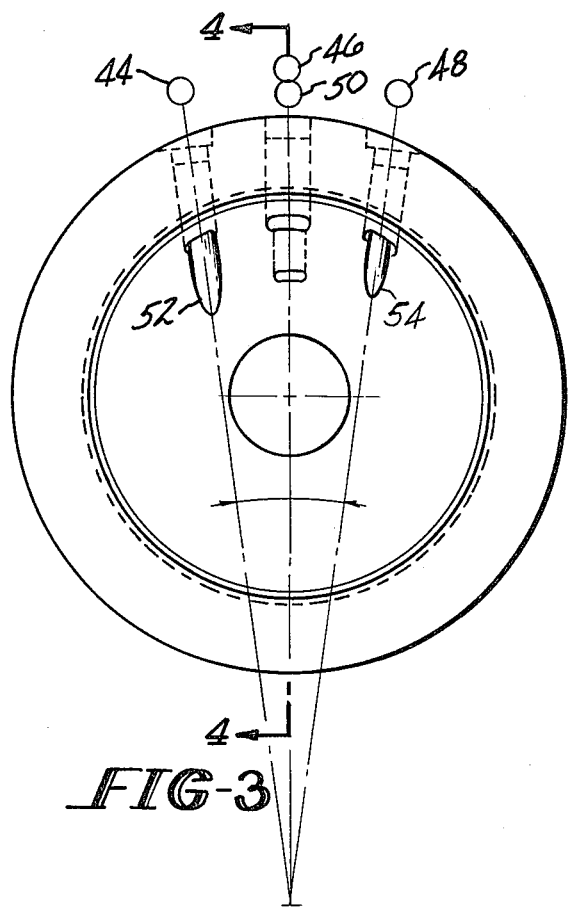
FIG. 3 is an end view of a half cell.
Figure 4:
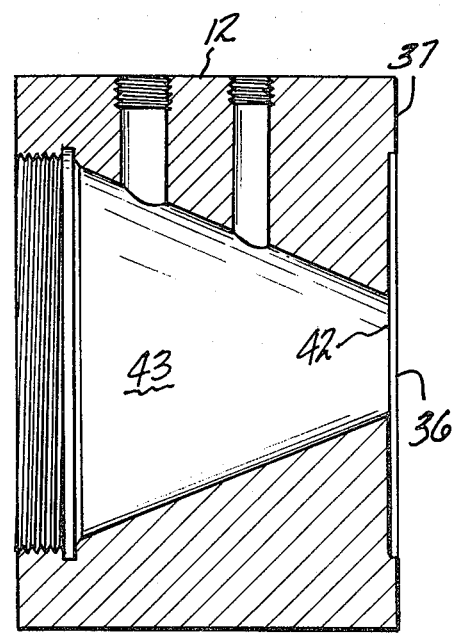
FIG. 4 is a cross sectional view of the half cell of FIG. 3 taken along the line 4—4.
Figure 6:
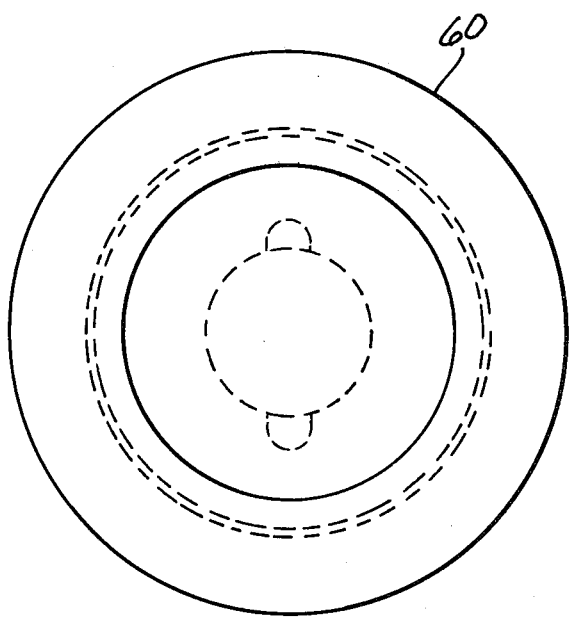
FIG. 6 is a plan view of cap as used in the half cell of FIG. 3.
Figure 5:
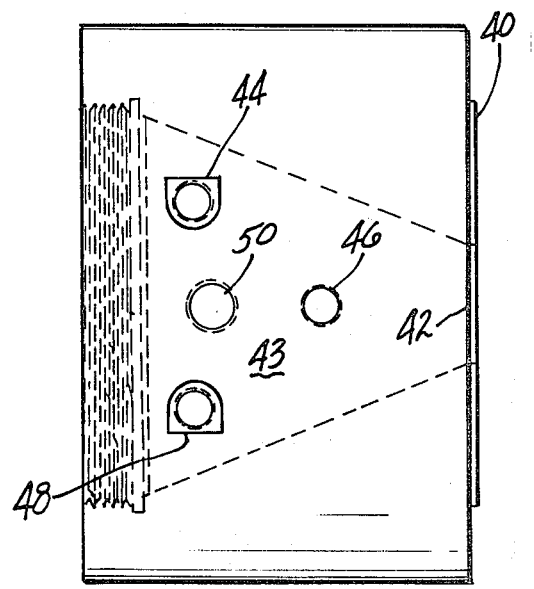
FIG. 5 is an outside top view of the half cell of FIG. 3.
Figure 8:
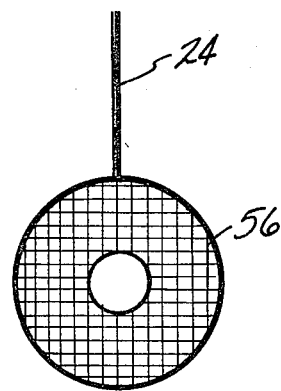
FIG. 8 is a plan view of a typical electrode as used in the invention of FIG. 1.
Figure 7:
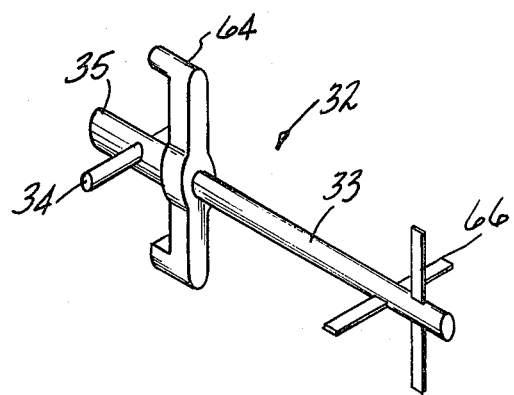
FIG. 7 is an isometric view of a stirrer assembly as used in the half cell of FIG. 3.

FIG. 1 shows an isometric view of a preferred embodiment of a membrane test cell 10 according to the present invention. As shown, it comprises two half cells 12 and 14 which are clamped together by end plates 16 and held in place with a plurality of double ended bolts 18. Ease of assembly and disassembly is assured by the use of wing nuts 20, although other tigtening methods could be used. When fully assembled, heater leads 26 and temperature sensor leads 28 are attached to each half cell, along with drying tubes 22 and electrode leads 24. Mounted externally onto each end is a stirrer motor 30 which is magnetically coupled to an internal stirrer 32 by one of a pair of permanent magnets 34, the other of which is located on the rear end 35 of stirrer shaft 33. All of this is shown generally in FIG. 2, which is an exploded cross sectional view of cell 10, and in FIGS. 3-9 which are detailed views of the major components thereof, to which reference should now be made.

In the preferred embodiment, the half cells are made from an inert, easily machinable polymeric material such as polytetrafluoroethylene, sold under the trademark Teflon ®, by the E. I. duPont Company. They are structurally identical except that left cell 12 has a slight cavity 36 cut into its inner face 37 into which a membrane 38 is fitted. When the two half cells are mated, a matching extension 40 in right half cell 14 fits into cavity 36 to clamp the membrane in place and seal the opening 42 between the two half cells. The unit is adaptable to use membranes such as those made from perfluorinated polymers having lateral functional side chains such as carboxylic, sulfonic or phosphonic acid groups, such membranes being available and identified by the trademarks NAFION and FLEMION. Sealing is abetted by one or more silicone gaskets (not shown) which hold the membrane firmly in place while keeping the assembled cell leak tight. As shown, each half cell is externally configured as a horizontally disposed cylinder having an inwardly directed truncated conical inner chamber 43 cut internally therein. When the two half cells are joined, the openings at truncated apex 42 are aligned and abut each other to form a biconic dumb bell shaped electrolytic cell. Although cell size is not especially critical, a typical cell is about 150 mm in diameter and 225 mm long. For this configuration, the gross volume of each half cell chamber 43 is about 500 cm$^3$.

Machined into the wall of each half cell are a set of four ports, 44, 46, 48 and 50, respectively, with ports 44 and 48 holding temperature sensor 52 and cartridge heater 54, respectively. Since both the sensor probe and heater are susceptible to solution corrosion damage, corrosion resistant container metal tubes (not shown) which are sealed at one end are first placed into the ports and the sensor probes and heaters then inserted into the tubes. Type 316 stainless steel is used for sodium hydroxide solutions while titanium is preferred for sodium chloride solutions. The tubes are fixed with threaded Teflon ® or similar fittings (not shown) which screw into and seal the entry ports. In use, an 80 watt cartridge heater placed in each half cell is used to heat the solutions; temperature control to ±1° C. being achieved by the use of a platinum temperature sensor and a proportional temperature controller.

In a preferred embodiment, one of a pair of matched circular platinum mesh electrodes 56 are held in each half cell in ports 46. For the purposes of transport number measurement, platinum is the preferred electrode material but the unit is readily adaptable to use advanced anodic and catalytic cathodes for more advanced experiments. The electrode leads are Teflon ® covered and, as with the thermal tubes, are fixed with threaded fittings which are screwed into the port openings to seal them. In a typical design, the electrodes are approximately 6 cm in diameter, and have a 1 cm center hole cut therein to allow stirrer shaft 35 to pass therethrough so that stirrer 32 can be extended to near the surface of membrane 38. Ports 50 are used to fill the chambers and for sample withdrawal, with weighed drying tubes 22 filled with molecular sieves being fitted to them so that water loss by evaporation can be determined.

Each half cell is closed at its outer end by an end cap 60 which, preferably, screws into the endmost portion of chamber 43. As shown, it has a hollowed out portion 62 into which stirrer magnet 34 and holder bearing 64 are mounted. While stirring speed is not critical, it has been found that the solutions should be stirred preferably at about 500-600 rpm to avoid concentration polarization at the membrane surfaces and to hasten thermal equilibrium. The application of this stirring taken in conjunction with the other unique structural features of the cell is a major reason for the improved test measurement accuracy observed. As with the other internal features of the cell, the stirrer blades 66, shaft 33, holder bearing 64 and magnet 34 of stirrer 32 are all Teflon ® covered.

Figure 9:
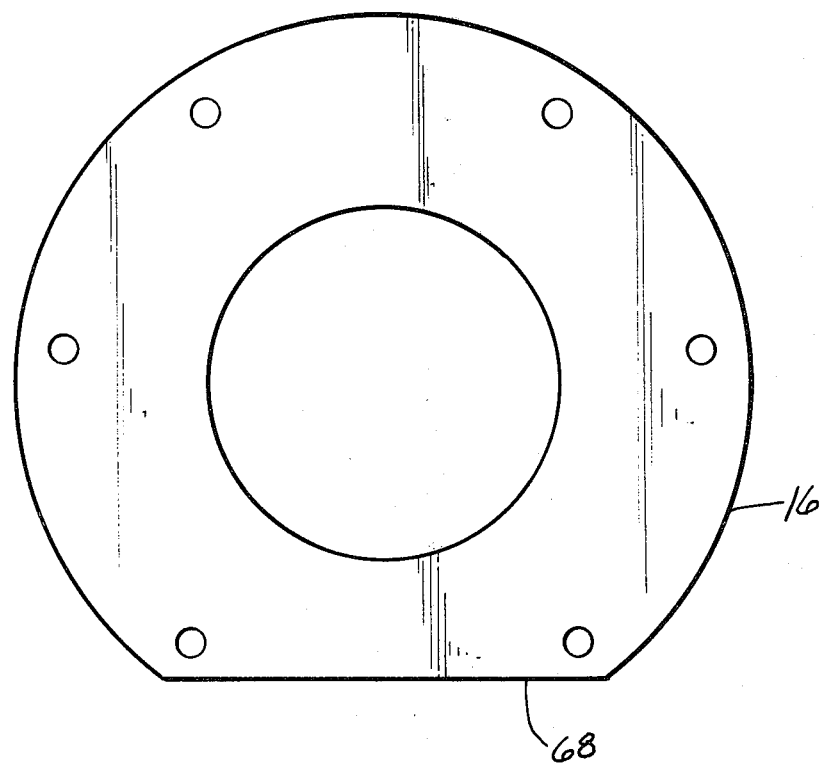
FIG. 9 is a plan view of an end plate as used in the invention of FIG. 1.

The cell is assembled by merely inserting a membrane and gasket between a left and right half cell, press fitting them together, placing an end plate 16 outside each end and tightening up bolts 18 with wing nuts 20. As shown in FIG. 9, plates 16 have flats 68 which allow the finished cell to be laid out horizontally as shown in FIG. 1.

Improved experimental accuracy is the result of all of these features. The conical chamber in each half cell provides for uniform current density distribution through the membrane, optimum drainage for solution recovery and gas bubble disengagement space above the solution level. Secondly, efficient stirring at the membrane faces coupled with precise temperature control eliminate problems with variable electrolyte concentration and membrane activity. Thirdly, the use of a radioactive tracer in conjunction with the cell design allows experiments to be more quickly and accurately performed than with previous apparatus and procedures.

EXAMPLES

Examples 1-17, summarized in the attached table, illustrate the scope and variety of cell conditions which can be used for the measurements of interest. In these Nafion ® 1150 equivalent weight and Nafion ® 295 fabric backed membrane were used, although any membrane type could have just as easily been employed.

Test cell 10 is designed to enable measurement of two membrane quantities: the fraction of current in an electrolysis cell which is carried by metallic cations (in this case sodium) through the membrane ($t_{Na+}$, mol Na+/Faraday of electricity) and the amount of water which is carried through the membrane per unit quantity of electrical current ($t_{H_2O}$, mol H$_2$O/Faraday).

After assembly of the cell as hereinabove described, the membrane is equilibrated with appropriate solutions at the preselected test temperatures generally between 70° and 90° C. in the cell for up to 24 hours. These solutions are then carefully removed by syphoning or other suitable method and replaced with weighed portions of identical solutions, about 330 ml being required for each half cell. Weighed drying tubes are then mounted onto ports 50 and stirring commenced.

After temperature equilibrium is achieved (about one hour), a sample of anolyte (about 1–2 grams) is withdrawn, weighed and titrated for either chloride or hydroxyl ion, depending on the sample. Then, about 30–60 microcuries of carrier free sodium-22 tracer is added to the anolyte, stirred and another sample taken to determine the initial level of activity. If the catholyte is of a different composition, a reference sample is also taken at this time.

Once these samples are taken, electrolysis is begun. The cell is designed to operate with current densities up to 5 KA/m² although 2–3 KA/m² are normally used. In the embodiment shown, the exposed membrane area is about 8 cm², so a current of 1.6–2.4 A is required to achieve this. Electrolysis is continued at constant current for 1–3 hours or until solution concentrations have changed about 1% at which time the electrolysis current and heaters are turned off. The hot anolyte and catholyte solutions are then carefully removed from the cell and placed into preweighed vessels, which after cooling are reweighed.

Samples of catholyte are titrated for the appropriate anion and counted for sodium-22 activity; typically, 0.5% of the original sodium-22 is transferred. At this time, the original anolyte sample is recounted to establish the sodium-22 decay rate and drying tubes 22 reweighed.

1. Sodium ion transport number

The moles of sodium ion which are transported through the membrane during electrolysis are calculated from the original specific activity of the anolyte solution ($A_a$, counts/minute/gram solution), the specific activity of the catholyte solution, $A_c$, the original concentration of the anolyte solution, $C_a$, and the final weight of the catholyte solution, $W_{cf}$.

$$\text{mol}_{Na+} = \frac{C_a}{A_a}(A_c W_{cf})$$

The sodium ion transport number is then calculated from the equation:

$$t_{Na+} = \frac{(\text{mol}_{Na+})(96,487)}{[i(\text{amp})][t(\text{seconds})]}$$

2. Water transport number

First the moles of salt in the final catholyte solution are calculated from the weight and concentration of that solution. Then the weight of water is calculated. Finally, the weight of water in the original catholyte solution is calculated in similar fashion and the difference, $\Delta w$, is determined. The transport number of water is calculated from the equation:

$$t_{H2O} = \frac{(\Delta w)(96,487)}{(18.01)[i(\text{amp})][t(\text{seconds})]} + 1$$

The second term is present to correct for the amount of water consumed in the electrode reaction during the electrolysis.

3. Estimates of precision

It is estimated that the precision of $t_{Na+}$ is ±0.015, and for the $t_{H2O}$ the precision is ±0.5 mol H₂O Faraday.

| | | | Sodium Ion and Water Transport Numbers* | | | |
|---|---|---|---|---|---|---|
| Example | Membrane | Temp, °C. | Anode Solution | Cathode Solution | $t_{Na+}$, mol/F | $t_{H2O}$, mol/F |
| 1 | 1150 | 70 | 5.0 M NaCl | 5.0 M NaCl | 0.99 | 3.6 |
| 2 | 1150 | 80 | 5.0 M NaCl | 5.0 M NaCl | 0.96 | 4.8 |
| 3 | | 90 | 5.0 M NaCl | 5.0 M NaCl | 1.00 | 2.3 |
| 4 | 1150 | 80 | 9.5 M NaOH | 9.5 M NaOH | 0.64 | 0.51 |
| 5 | | 80 | 11.0 M NaOH | 11.0 M NaOH | 0.61 | 0.56 |
| 6 | | 80 | 12.5 M NaOH | 12.5 M NaOH | 0.56 | 0.51 |
| 7 | 1150 | 90 | 9.8 M NaOH | 9.8 M NaOH | 0.64 | 0.51 |
| 8 | | 90 | 13.0 M NaOH | 13.0 M NaOH | 0.60 | 0.87 |
| 9 | 1150 | 80 | 5.0 M NaCl | 9.5 M NaOH | 0.69 | 1.9 |
| 10 | | 80 | 5.0 M NaCl | 11.0 M NaOH | 0.62 | 1.9 |
| 11 | | 80 | 5.0 M NaCl | 12.5 M NaOH | 0.58 | 1.7 |
| 12 | 295 | 80 | 9.5 M NaOH | 9.5 M NaOH | 0.96 | 1.8 |
| 13 | | 80 | 11.0 M NaOH | 11.0 M NaOH | 0.94 | 1.4 |
| 14 | | 80 | 12.5 M NaOH | 12.5 M NaOH | 0.83 | 1.4 |
| 15 | 295 | 80 | 5.0 M NaCl | 9.5 M NaOH | 0.94 | 2.9 |
| 16 | | 80 | 5.0 M NaCl | 11.0 M NaOH | 0.96 | 3.0 |
| 17 | | 80 | 5.0 M NaCl | 12.5 M NaOH | 0.88 | 2.9 |

*Current density = 2.0 KA/m².

The invention may be embodied in other specific forms without departing from the spirit or essential characteristics thereof. The present embodiment is considered to be in all respects as illustrative and not restrictive, the scope of the invention being indicated by the appended claims rather than the foregoing description and all changes which come within the meaning and range of equivalency of the claims are therefore intended to be embraced therein.

What is claimed is:

1. An electrochemical membrane test cell comprising:
   a pair of half cells, each containing a horizontally disposed, inwardly directed, truncated right conical chamber, said cell being formed by joining said half cells at their truncated apexes so that said truncated chambers are aligned and abut each other to form a biconic electrolytic cell;
   electrode means within each half cell, said means being adapted to be an anode in one of said pair of half cells and a cathode in the other of said pair;
   permselective membrane means, said membrane being sealingly suspended between said half cells, so that said cell is separated into an anodic and a cathodic compartment;

stirring means within each half cell, said means being extended to be close to the surface of said membrane means;

heating means within each of said compartments; and electrolyte introduction means within each of said compartments, said cell being adapted to perform electrochemical studies to measure the water and metallic cation transport numbers for said membrane means.

2. The apparatus of claim 1 wherein said half cells are made from an inert material.

3. The apparatus of claim 2 wherein said inert material is polytetrafluoroethylene.

4. The apparatus of claim 1 wherein a first of said pair of half cells has a cavity in its inner face, said cavity being adapted to receive said membrane means, and the second of said pair of half cells has an extension which is adapted to fit into said cavity and sealingly engage said membrane, said sealing being abetted by an inner gasket adapted to clamp said membrane in place and keep the joined half cells leak tight.

5. The apparatus of claim 4 wherein said membrane means comprises a membrane made from a perfluorinated polymer having lateral side chains, said side chains selected from the group consisting of carboxylic, sulfonic and phosphonic acid functional groups.

6. The apparatus of claim 5 wherein said membrane has carboxylic acid functional side groups.

7. The apparatus of claim 5 wherein said membrane has sulfonic acid functional side groups.

8. The apparatus of claim 1 wherein said electrode means is a pair of platinum mesh electrodes, one in each half cell.

9. The apparatus of claim 1 wherein said electrode means comprises a dimensionally stable anode and a catalytic cathode.

10. The apparatus of claim 1 wherein said cell is adapted to operate with a current density up to 5 $KA/m^2$.

11. The apparatus of claim 10 wherein said cell is adapted to operate with a current density of 2–3 $KA/m^2$.

12. The apparatus of claim 1 wherein said heating means comprises a cartridge heater and temperature sensing and control means adapted to maintain the temperature of said electrolyte to $\pm 1°$ C.

13. The apparatus of claim 12 further comprising a plurality of corrosion resistant container tubes adapted to sealingly engage the wall of said half cell, said tubes being sealed at their innermost ends and being adapted to hold said heater and sensing means and protect them from corrosion damage from said electrolyte.

14. The apparatus of claim 12 wherein said heater is adapted to heat said electrolyte to a temperature of up to 100° C.

15. The apparatus of claim 1 wherein said cell is adapted to operate with concentrations of chloride or caustic of up to 45% in said electrolyte.

16. A method of measuring metallic cation and water transport numbers for cation exchange hydraulically impermeable membranes comprising:

forming a cell, said cell comprising two half cells, each of said half cells containing an internal horizontally disposed, inwardly directed, truncated right conical inner chamber, said cell being formed by joining said half cells at their truncated apexes so that said truncated chambers are aligned and abut each other to form a biconic electrolytic cell, said half cells having one of said membranes sealingly suspended therebetween to form an anode and a cathode compartment, each of said compartments having electrode means, heating means, sensing means, stirring means and electrolyte introduction means;

filling said anode and cathode compartments with anolyte and catholyte solutions and heating said solutions to equilibrate said membrane at a preselected test temperature;

removing said solutions and replacing them with weighed portions of the same solutions;

adding a measured amount of radioactive tracer material to said anolyte solution;

heating and stirring said solutions to achieve a uniform concentration of said anolyte and tracer;

energizing said electrode means to electrolyze said solutions for a period of time, said electrolysis producing a transfer of said tracer material through said membrane into said cathode compartment;

at the conclusion of said electrolysis period, measuring the quantity of tracer which has passed through said membrane; and measuring the net change in the water content of the electrolyte in each compartment, said quantities being indicative of the moles of metallic cation and water which have been transferred.

17. The method of claim 16 further comprising adding weighed drying tubes to the inlet means of said half cells, said drying tubes acting to capture any water evaporated during said electrolysis period.

18. The method of claim 16 further comprising the steps of:

taking a sample of said anolyte solution prior to the introduction of said tracer and analyzing it for anion content;

taking samples of said anolyte and catholyte solutions after said tracer has been added and counting them for initial levels of activity before electrolysis has begun;

after electrolysis is complete, removing said anolyte and catholyte solutions from said cell, transferring them to preweighed containers and weighing them;

measuring the cation content and final tracer activity of said catholyte solution;

recounting said unelectrolyzed anolyte sample to establish the level of tracer decay; and reweighing said drying tubes.

19. The method of claim 18 wherein said tracer element is sodium-22.

20. The method of claim 16 wherein said electrolyzing is performed at a current density of up to 5 $KA/m^2$.

21. The method of claim 20 wherein said electrolyzing is performed at a current density of 2–3 $KA/m^2$.

22. The method of claim 16 wherein said electrolyte is heated up to about 100° C.

23. The method of claim 22 wherein said heating is controlled to $\pm 1°$ C.

* * * * *